United States Patent [19]

Dailey

[11] 4,082,094
[45] Apr. 4, 1978

[54] LOCKING DEVICE FOR INTRAVENOUS INSERT

[76] Inventor: Calvin L. Dailey, 884 6th St., Petaluma, Calif. 94952

[21] Appl. No.: 723,047

[22] Filed: Sep. 13, 1976

[51] Int. Cl.² .............................................. A61M 5/00
[52] U.S. Cl. .............................. 128/214 R; 128/133; 128/221; 285/421; 24/260
[58] Field of Search ............. 128/214 R, 214.2, 214.4, 128/221, 133, DIG. 16; 24/260; 285/421

[56] References Cited

U.S. PATENT DOCUMENTS

| 2,707,953 | 5/1955 | Ryan | 128/214 R |
| 2,928,391 | 3/1960 | Krug | 128/214 R |
| 3,186,744 | 6/1965 | Smith et al. | 285/421 |
| 3,537,451 | 11/1970 | Beck et al. | 128/214.4 |
| 3,834,380 | 9/1974 | Boyd | 128/214 R X |
| 3,853,130 | 12/1974 | Sheridan | 128/349 R |
| 3,856,009 | 12/1974 | Winnie | 128/214.4 |

Primary Examiner—Dalton L. Truluck
Attorney, Agent, or Firm—Flehr, Hohbach, Test, Albritton & Herbert

[57] ABSTRACT

A locking device for a tubing connection used in intravenous feeding. The invention comprises a body with a channel therein adapted to receive a tubing connection. The body is resiliently compressible transverse to the channel. To secure the locking device against a tubing connection, the body is compressed and a retainer installed. Once in place, the locking device prevents separation of the intravenous tubing connection between a vein insert tube and the termination of an intravenous supply tube. Installation and removal of the locking device is readily effected, thus permitting secure connection and ready separation of an intravenous fluid line without pulling or twisting.

8 Claims, 10 Drawing Figures

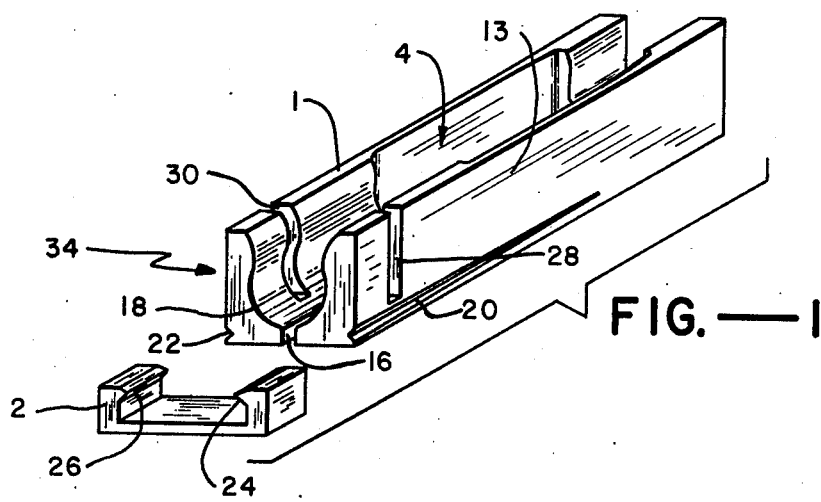
FIG.—1
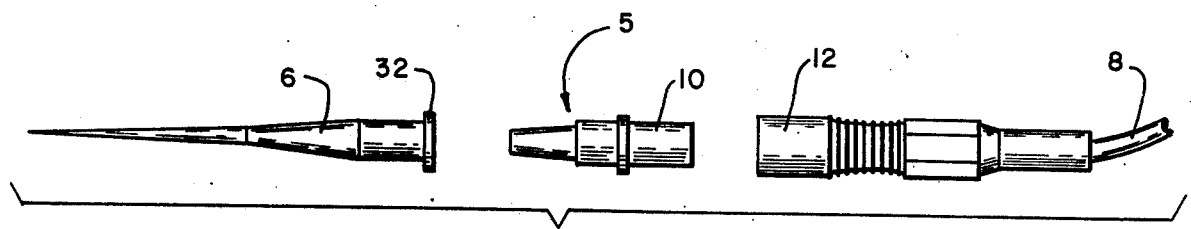
FIG.—2
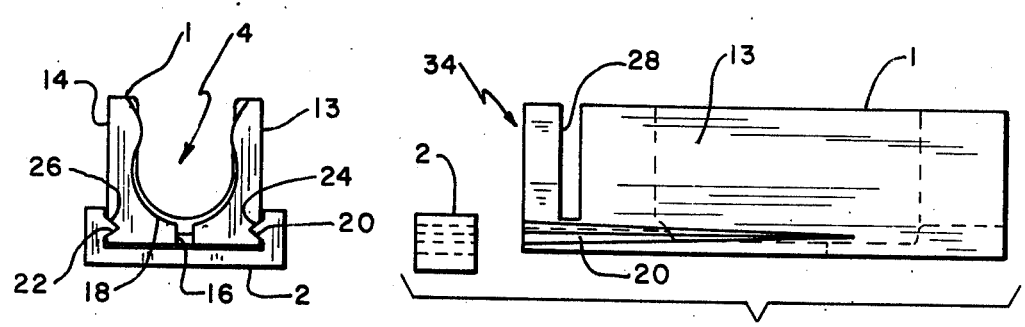
FIG.—3
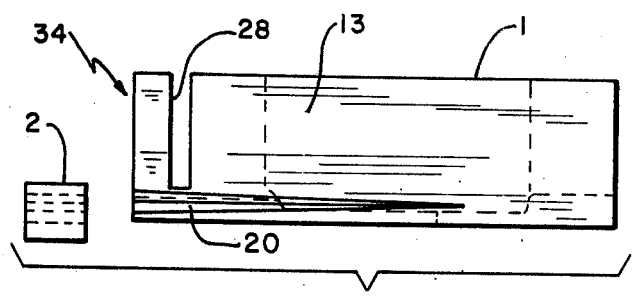
FIG.—4
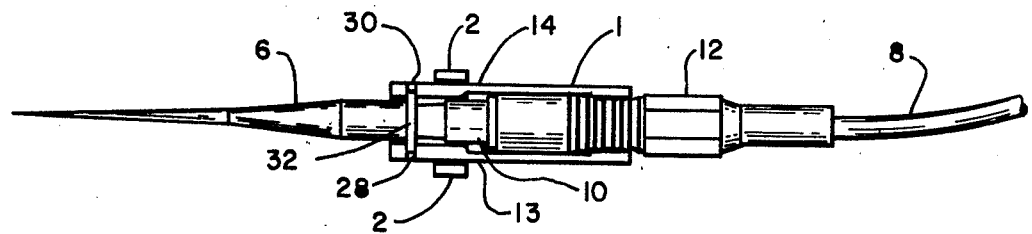
FIG.—5

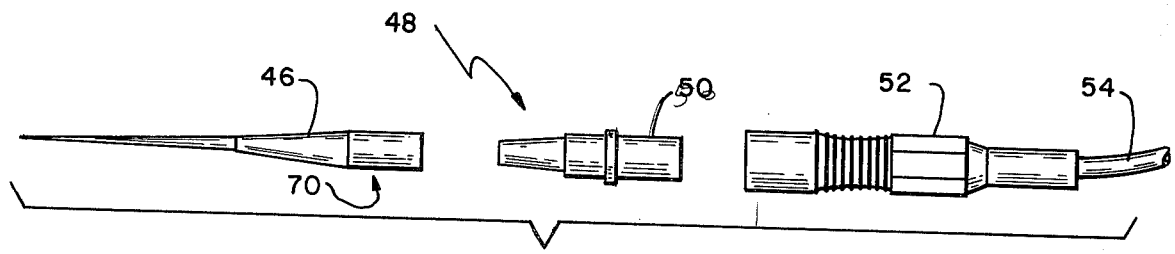
FIG.—6
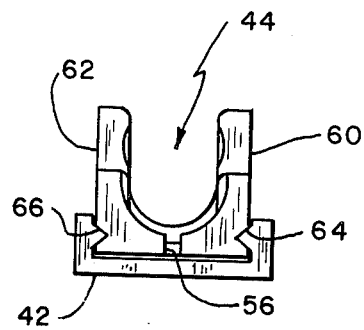
FIG.—7
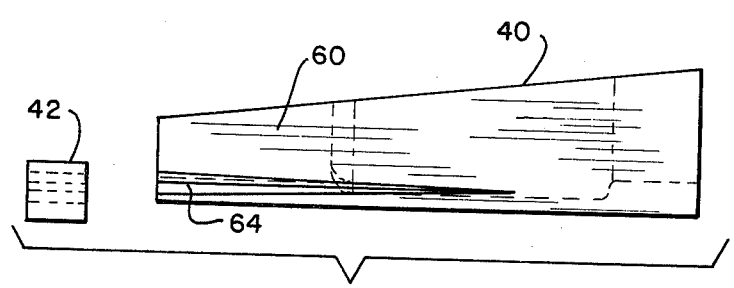
FIG.—8
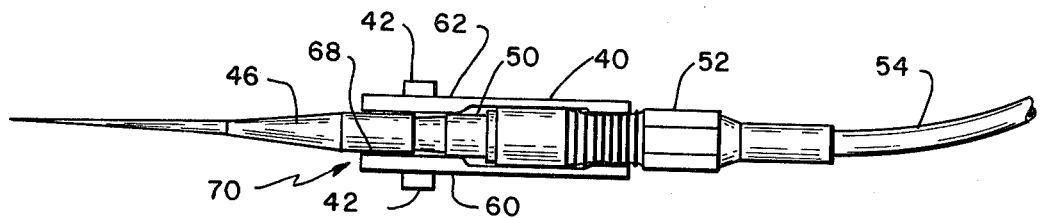
FIG.—9
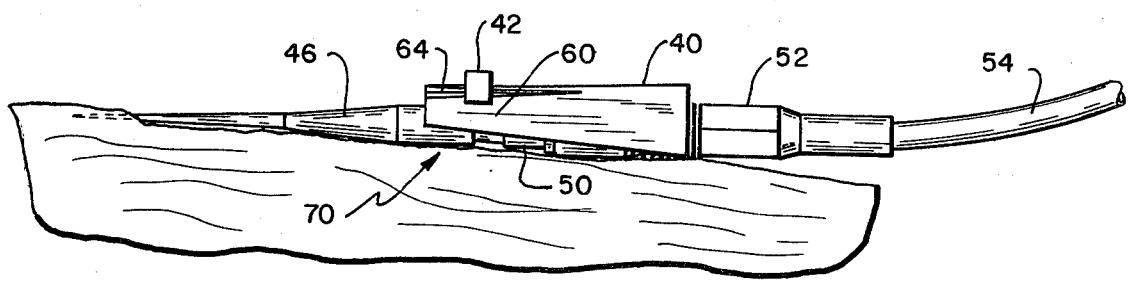
FIG.—10

LOCKING DEVICE FOR INTRAVENOUS INSERT

BACKGROUND OF THE INVENTION

The present invention relates generally to releasable tubing connections used in intravenous feeding, and more particularly to a locking device or holder adapted to prevent separation of the tapered plastic vein insert from the intravenous supply.

The most common method of intravenous feeding requires the installation of a long tapered insert into a vein with the aid of a hypodermic needle. The insert, which is conventionally formed of plastic or other flexible material, is first installed over the needle, and then inserted in a vein. Once in place, the needle is withdrawn, leaving the insert in place. Intravenous supply tubing is then connected to the insert. Because the insert must be installed in the vein independently, the connection between intravenous supply and insert cannot be permanent. Present means for effecting the connection generally provide for insertion of the forward end of the intravenous supply line into the back of the insert tube, with the connection being maintained by friction. A difficulty with the standard connection is the potential for separation due, for example, to patient movement, thus allowing intravenous fluid and the patient's blood to soil bedclothes. Temporary interruption of the nutrient supply, or loss of blood, might also pose a serious health risk to the patient.

Because any excessive movement of the tapered insert is likely to cause patient discomfort, a ribbed or twist-type connector lock is undesirable.

There is, therefore, need for a conveniently installed, releasable means to secure the connection between a vein insert and supply tube of an intravenous feeding system without excessive pulling or twisting.

SUMMARY AND OBJECTS OF THE INVENTION

The invention discloses a locking device for a tubing connection used in intravenous fluid supply which may be readily installed and released without pulling or twisting. The body of the locking device is provided with a channel adapted to receive the conventional tubing connection between a tapered vein insert tube and a cooperating connector at the termination of an intravenous supply tube. The body is formed to be resiliently compressible transverse to the connection channel. Through use of cooperating means, the interior dimension of the channel can be selectively reduced. When the tubing connection is placed in the channel, and transverse compression is applied, the tubing connection is held in the body so as to prevent separation.

In general it is an object of this invention to provide an improved means for assuring the continuity of an intravenous supply.

Another object of this invention is to provide a locking device to secure the connection between a vein insert and an intravenous supply tube.

Another object of this invention is to provide a locking device of the above character which may be readily assembled in place, or removed without pulling or twisting.

Additional objects and features of the invention will appear from the following description in which preferred embodiments have been set forth in detail in conjunction with the accompanying drawings.

BRIEF DESCRIPTION OF THE DRAWINGS

FIG. 1 is a perspective view of one embodiment of a locking device according to the invention, shown in disassembled form.

FIG. 2 is an exploded view on a reduced scale, of an intravenous tubing connection capable of being held and received within the locking device of FIG. 1.

FIG. 3 is an end view of the locking device of FIG. 1, shown in assembled form.

FIG. 4 is a side view of the locking device shown in FIG. 1.

FIG. 5 is a bottom plan view of the locking device of FIG. 1, showing the locking device and retained tubing connection in assembled condition.

FIG. 6 is an exploded view, similar to FIG. 2, of another form of an intravenous tubing connection.

FIG. 7 is an end view similar to FIG. 3, of another embodiment of a locking device according to the invention.

FIG. 8 is a side view, similar to FIG. 4, of the locking device of FIG. 7.

FIG. 9 is a bottom plan view similar to FIG. 5, showing the locking device of FIGS. 7 and 8 and the tubing connection of FIG. 6 in assembled condition.

FIG. 10 is a side view of the assembled device of FIG. 9 in place adjacent the skin.

DESCRIPTION OF THE PREFERRED EMBODIMENT

One embodiment of a locking device according to the present invention shown in FIGS. 1, 3 and 4, and includes a body 1 and retainer 2. The body 1 has a channel 4 therein which is adapted to receive a tubing connection 5, such as the one shown in exploded form in FIG. 2. The locking device is generally employed to firmly but releasably hold and secure the tubing connection which, as illustrated, is between a vein insert and supply tubing for intravenous fluid. Channel 4 can be shaped or contoured along its length, and extends from one end to the other of body 1.

As illustrated in FIG. 2, the tubing connection 5 generally comprises the junction between a first tapered tube 6 which is insertable into a vein, and supply tubing 8 for intravenous fluid. The supply tubing 8 includes a connecting tubular member 10, which can be inserted and frictionally engaged within the vein insert tube 6, and a flexible tubular member 12 which serves as a juncture at the end of the supply tube 8 for intravenous fluid. Preferably the channel 4 is shaped or contoured to generally conform to the configuration of the tubing connection 5, and is of sufficient length to receive the connecting portions of the insert tube 6, the connecting tubular member 10 and at least a portion of the flexible tubular member 12. This will increase the gripping surface available to the locking device and make it easier to position and install.

To facilitate holding the tubing connection within the locking device, the body 1 can be formed of any suitable material such as plastic or the like, (e.g., molded polyethylene or polypropylene), making it resiliently compressible transverse to the channel 4. In general, the material should be sufficiently resilient so that side portions 13 and 14 of the body can be compressed to hold the tubing connection 5 firmly within the channel 4. To improve transverse compressibility, groove means 16 can be provided in a lower surface of the channel 4, at one end and penetrating the lower portion 18 of the body (see FIG. 1). This will permit the side portions 13 and 14 of the body to be forcibly depressed toward one another. As illustrated, the groove means 16, which may be in the form of a slot or gap in the bottom of the channel 4, has a longitudinal dimension which is at least half the length of the body 1. In general, the groove means 16 permits resilient materials of increased rigidity to be used in forming the body. For example, a plastic material which might otherwise be insufficiently resilient to permit required transverse compressibility can be employed.

The desired locking function is achieved by applying transverse compression on side portions 13 and 14 of the body, while the tubing connection 5 is in place within the channel 14, to thereby reduce the interior dimension of the channel. While finger pressure or other means may be used to initially obtain such transverse compression, the locking device of the present invention additionally includes means for maintaining the transverse compression, once applied. In the embodiment of FIGS. 1-5, such means is in the form of a releasable clamp or retainer 2 of generally C-shaped configuration. As shown in FIGS. 1, 3 and 4, the retainer 2 is slidably movable onto the body 1 to maintain transverse compression on the sides 13 and 14 of the body. For such purpose, additional groove means 20 and 22 are provided on the outside of the body 1, on each side of the groove means 16 to serve as channels in which the retainer 2 (serving as a releasable clamp means), may slidably engage. Thus, as particularly shown in FIGS. 1 and 3, the retainer 2 has inwardly projecting surfaces or flanges 24 and 26, adapted to engage within the additional grooves 20 and 22 to hold the retainer 2 on the body 1.

To further inhibit longitudinal movement or separation of the tubing connection described above, the body 1 can be provided with additional groove means arranged transverse to the channel 4, in the form of vertically extending slots 28 and 30. The insert tube 6 can be suitably provided with a cooperating transverse ridge 32, engagable within the groove means 28 and 30. As illustrated, the transverse ridge 32 can be in the form of a radially extending flange of a dimension or width slightly less than that of the slots 28 and 30.

Because the above-described embodiment employs a slot or similar groove means 16 penetrating the bottom 18 of the channel 4, when the retainer 2 is in place, the body 1 exhibits a slight taper. This taper results from transverse compression which, when applied to sides 13 and 14 of the body, forceably depresses the sides toward one another to thereby reduce the width of the groove means 16 and, also, of the channel 4 in that end 34 of the body 1. By also providing a slight taper to the exterior grooves 22 and 24, the retainer 2 may serve the additional function of increasing the transverse compression applied to the body 1. This is because the retainer 2, functioning as a clamp means, is movable from an outward position to an inner position. In the outward position, the body portions on either side of the groove means 16 are forcibly depressed toward one another but remain relatively spaced from one another. In an inner position, they are further depressed toward one another into a locking position whereby the tubing connection is held within the shaped channel 4 of the body 1. Such locking function occurs as the retainer 2 is slid along side grooves 22 and 24, away from the outer end 34 of the body, to thereby reduce the interior channel dimension so that the channel surfaces squeeze and hold the tubing connection together in place. While the described function is enhanced by tapering the grooves 22 and 24, such taper is not essential as compression can be accommodated by the groove 16 and, to some extent, within the resilient material of the body.

To use the locking device in conjunction with an intravenous fluid supply, the insert 6 must first be installed in a vein. This is most commonly done by placing it over a hypodermic needle. Both the needle and insert 6 are then inserted into a vein, and the needle is withdrawn. The supply tubing for intravenous fluid 8 is then frictionally mated with the insert 6 to form the tubing connection 5. To secure this connection, the locking device of this invention is installed over the tubing connection 5. It is positioned such that the ridge 32 on the insert fits within the transverse slots 28 and 30. Generally, the locking device is inverted over the tubing connection 5, the latter remaining adjacent the skin. It thus serves as a shield for the connection 5. Once the connection 5 is in place, the retainer 2 is installed by pressing the sides 13 and 14 of the body 1 together and sliding the retainer 2 over the end 34 of the body so that the flanges 24 and 26 pass into the grooves 20 and 22. When the retainer 2 has moved sufficiently far inward, the locking device will securely hold the tubing connection 5 within the channel 4, so that the insert tube 6 and the supply tubing for intravenous fluid 8 will not separate. If additional compression on the connection is needed or desired, the retainer 2 may be moved further along the body 1, as outlined above.

FIGS. 7-10 illustrate another embodiment or a locking device for an intravenous supply connection, according to the present invention.

In general, the embodiment of FIGS. 7-10 comprises a body 40, with a shaped channel 44 therein, and a retainer 42. The channel 44 extends along the length of the body 40 and is preferably contoured to substantially conform to the shape of the tubing connection to be secured. As in the embodiment of FIGS. 1-5, the channel 44 is adapted to reveive the tubing connection between a tube insertable into a vein and supply tubing for intravenous fluid.

Referring to FIG. 6, a tubing connection 48 is shown in exploded form. The tube 46, of substantially the same character and function as the insert tube 6 of the first embodiment, can be of conventional design except for omission of the transverse ridge 32. The supply tubing for intravenous fluid can similarly comprise a connection tubular member 50 adapted to frictionally engage the insert tube 46 and a flexible tubular member 52 which serves to join the connector 50 to a supply conduit 54 leading to a source of intravenous fluid.

As in the first embodiment, the channel 44 will preferably be of sufficient length to receive both the connection between the insert tube 46 and the connecting tubular member 50 and at least a portion of the flexible tubular member 52.

As in the first embodiment, the body 40 is resiliently compressible transverse to the channel 44. To facilitate transverse compressibility, groove means 56, penetrating a lower surface 58 of the channel 44, is provided. It is again recommended that this groove means 56 be in the form of a slot or gap, preferably extending over half the length of the body 40.

The embodiment of FIGS. 7-10 also includes means for maintaining transverse compression on side portions 60 and 62 of the body sufficient to hold and secure the tubing connection 48 within the channel. A releasable clamp means, in the form of a generally C-shaped retainer 42 is similarly designed to engage exterior grooves 64 and 66 in the body 40. The retainer 42 can be slidably engaged on the body 40 to serve as the means for maintaining transverse compression, in the manner previously described.

Although not an essential requirement for this invention, it is preferred that the portion 68 of the shaped channel 44 adapted to receive the end 70 of the insert 46, closely conform to the dimensions of the insert 46. Less transverse compression will then be required to effect a tight, secure hold on the tubing connection 48, to prevent its separation.

Use of the embodiment of the locking device shown in FIGS. 7-10 is essentially the same as for the first embodiment. After the vein insert 46 is in place and the cooperating tubular member 50 is frictionally mated with it, the body 40 is placed over the connection 8 and the retainer 42 installed as shown in FIG. 10. Transverse compression maintained by the retainer 42 serves to hold the tubing connection 48 within the channel to insure that the insert tube 46 and the supply tubing 54 for intravenous fluid will not separate.

Other embodiments of locking devices including variations in the means of maintaining transverse compression are clearly within the scope of this invention. Thus a retainer and groove means of the type disclosed above can be arranged so that a retainer can be slidably attached to the top of the body, rather than to the bottom, and thereby position the tubing connection between the body channel and retainer. The retainer construction might also be such that the retainer is slid or snapped onto protruding ridges on the outer surface of the body. It should therefore be understood that while particular embodiments of a locking device have been described, various modifications and changes may be made within the scope of this invention, as set forth in the appended claims.

I claim:

1. In a locking device for firmly but releasably holding a tubing connection between a vein insert and supply tubing for intravenous fluid, a body formed of resilient material, said body being provided with a shaped channel extending along its length, said body being compressible transverse to said channel whereby side portions of said body on each side of said channel can be forcibly depressed toward one another, and means for releasably applying compression on said side portions of said body to forcibly depress said side portions toward one another to engage and hold both the vein insert and the supply tubing within said shaped channel of said body.

2. A locking device as in claim 1 wherein said means for releasably applying compression on said side portions of said body includes a retainer slidably attached to said body.

3. A locking device as in claim 1 wherein said body includes groove means penetrating a lower surface of said shaped channel at one end of said body thereby facilitating the forcible depression of said side portions toward one another.

4. A locking device as in claim 1 wherein said vein insert has a radially extending flange and groove means are provided in said body transverse to said channel to receive said flange.

5. In a locking device for firmly but releasably holding a tubing connection between a vein insert and supply tubing for intravenous fluid, a body formed of resilient material, said body being provided with a shaped channel extending along its length, groove means penetrating a lower surface of said channel at one end of said body whereby portions of said body on each side of said groove means can be forcibly depressed toward one another, additional groove means on the outside of said body on each side of said first named groove means, and releasable clamp means slidably engagable in said additional groove means, said clamp means being movable from an outward position wherein said body portions are forcibly depressed toward one another but remain spaced from one another, to an inner position wherein said body portions are further depressed toward one another into a locking position by said clamp means, whereby said tubing connection is held within said shaped channel of said body.

6. A locking device as in claim 5 wherein said groove means penetrating the lower surface of said channel has a longitudinal dimension which is at least half the length of said body.

7. A locking device as in claim 5 wherein said releasable clamp means is generally C-shaped in configuration.

8. A locking device as in claim 5 wherein said vein insert has a radially extending flange and groove means are provided in said body transverse to said channel to receive said flange.

* * * * *